(12) United States Patent
Xing et al.

(10) Patent No.: US 9,382,194 B2
(45) Date of Patent: Jul. 5, 2016

(54) IODINATION PROCESS FOR THE PREPARATION OF 3, 5-DISUBSTITUTED-2, 4, 6-TRIIODO AROMATIC AMINES COMPOUNDS

(75) Inventors: Hongdeng Xing, Shanghai (CN); Lei Li, Shanghai (CN); Zhiqi Hu, Shanghai (CN)

(73) Assignee: IMAX Diagnostic Imaging Holding Limited, Wanchai, Hong Kong (CN)

( * ) Notice: Subject to any disclaimer, the term of this patent is extended or adjusted under 35 U.S.C. 154(b) by 0 days.

(21) Appl. No.: 14/355,396

(22) PCT Filed: Oct. 31, 2011

(86) PCT No.: PCT/CN2011/081546
§ 371 (c)(1),
(2), (4) Date: Aug. 29, 2014

(87) PCT Pub. No.: WO2013/063737
PCT Pub. Date: May 10, 2013

(65) Prior Publication Data
US 2015/0025275 A1    Jan. 22, 2015

(51) Int. Cl.
*C07C 231/12*    (2006.01)

(52) U.S. Cl.
CPC ............ *C07C 231/12* (2013.01); *Y02P 20/582* (2015.11)

(58) Field of Classification Search
CPC .......................... C07C 231/12; Y02P 20/582
USPC ................................................ 564/153, 156
See application file for complete search history.

(56) References Cited

U.S. PATENT DOCUMENTS

| 5,013,865 | A  | * | 5/1991  | Cross ................... C07C 237/46 560/37 |
| 5,698,739 | A  | * | 12/1997 | Sovak ................ A61K 49/0452 424/9.452 |
| 7,642,374 | B2 | * | 1/2010  | Yoshimura et al. ........... 562/494 |
| 2004/0082811 | A1 |   | 4/2004 | Anelli et al. |
| 2007/0219396 | A1 | * | 9/2007 | Yamada et al. ................ 562/456 |
| 2008/0146853 | A1 | * | 6/2008 | Midorikawa et al. ......... 570/206 |

FOREIGN PATENT DOCUMENTS

| JP | 2001-52667 A | 12/2001 |
| WO | 98/52908 A1 | 11/1998 |
| WO | WO 2010/121904 | * 10/2010 |

* cited by examiner

*Primary Examiner* — Shailendra Kumar
(74) *Attorney, Agent, or Firm* — MacMillan, Sobanski & Todd, LLC

(57) ABSTRACT

The invention discloses a improved process for the preparation of 3,5-disubstituted-2,4,6-triiodo aromatic amines of formula (II), wherein $R_1$ and $R_2$ are defined as herein. The compounds of formula (II) are the key intermediates for the synthesis of a series of non-ionic contrast agents such as Iopamidol, Iohexol and Iodixanol. The process comprises reacting chlorine-free iodinating reagents with 3,5-disubstituted-2,4,6-triiodo aromatic amines to obtain 3,5-disubstituted-2,4,6-triiodo aromatic amines of formula (II), wherein the molar yield of the iodination reaction can reach to 89%.

(II)

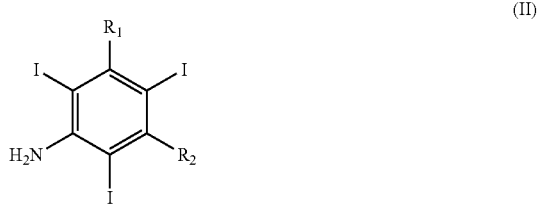

20 Claims, No Drawings

IODINATION PROCESS FOR THE PREPARATION OF 3, 5-DISUBSTITUTED-2, 4, 6-TRIIODO AROMATIC AMINES COMPOUNDS

The present invention claims the benefit of the PCT/CN2011/081546 filed Oct. 31, 2011.

TECHNICAL FIELD

The present invention relates to a process for the industrial scale preparation of poly-iodinated aromatic compounds. More particularly, it relates to industrial scale preparation of 3,5-disubstituted-2,4,6-triiodo aromatic amines. The key innovative point is the successful development of a new chlorine-free iodination system. Since 3,5-disubstituted-2,4,6-triiodo aromatic amines are key intermediates for the preparation of a series of iodinated non-ionic contrast agent, the present invention is relevant to the field of process technology in chemistry in the pharmaceutical industry. More particularly, it relates to the technical field of process technology for the production of iodinated non-ionic contrast agent.

BACKGROUND ART

During medical diagnosis using X-ray a large part of human tissues are not visible because of the low density and thickness difference of these tissues. It is therefore necessary to introduce a material which changes their absorptivity of X-rays in order to acquire a clearer image to confirm the veracity of the diagnosis. This material is called a contrast agent.

Elements with higher atomic number have increased photoelectric effects with X-rays. The range of the spectrum of the absorption frequency of X-rays by an element is largely dependent on its arrangement of the extra nuclear electrons. The frequency of the X-ray utilized for medical diagnosis is attuned to the X-ray absorption spectrum of the barium atom and the iodine atom. Therefore, these two elements create high density shadows during X-ray imaging.

Iodinated contrast agents are a series of compounds which are widely used in X-ray imaging diagnosis techniques. Second generation non-ionic contrast agents are currently and mainly utilized in clinical practice. These include, Iopamidol, Iohexol, Iopromide, Iomeprol, Iopentol and Ioversol. More recently developed dimer type non-ionic contrast agents have lower osmotic pressure and lower side effects. Two examples for this type of contrast agent are Iotrolan and Iodixanol.

The wide application of iodinated contrast agents results in their huge demand. This has prompted pharmaceutical enterprises all over the world to carry out a series of studies on the development and improvement of the synthetic process of this type of contrast agent.

It is obvious that the molecular backbone of these types of contrast agents share a tri-iodinated aromatic nucleus as shown in follow drawing:

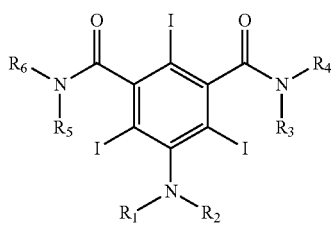

This structure illustrates that the ratio of the number of iodine atoms per molecule of the contrast agent is 3/1 for a monomeric agent or 6/1 for a dimer, which provides enhanced contrast effect. It is therefore obvious that 3,5-disubstituted-2,4,6-triiodo aromatic amines are key intermediates for the synthesis of this type of iodinated contrast agent in common synthetic routes.

The abundance of iodine in the nature is low. This means that iodine and its related compounds which are used as iodinating reagents are relatively expensive. Summing up the above, if an advanced process which is appropriate for the synthetic step shown in the following transformation could achieve high yield, reasonable consumption of the iodination reagent and a reasonable cycle time, it would have great significance on the industrial production of 3,5-disubstituted-2,4,6-triiodoaniline intermediates and subsequently the contrast agents themselves.

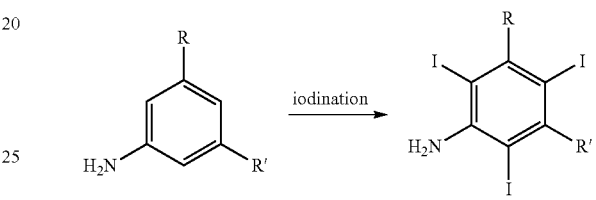

Development of the new iodination process would start at selecting an appropriate iodinating reagent. A system wherein the reagent is equivalent to the iodine cation (I$^+$) is required for this reaction and follows the well-known aromatic electrophilic substitution mechanism. A traditional method usually described in references and patents is using IX (iodine cation (I$^+$) mono-halide) as the iodination reagent. And there is no doubt that ICl is the most practical choice of this type of iodination reagent on an industrial scale.

Generally this type of process uses a solution of ICl in concentrated HCl as the iodination reagent to react with the aromatic nucleus of the substrates at about 90° C. The process disclosed in U.S. Pat. No. 5,013,865 (Mallinckrodt, Inc.) is a typical example. ICl reacts with water and is converted to hypoiodous acid and hydrogen chloride, but since this type of iodination reaction is usually carried out in aqueous media an alkali metal halide salts such as NaCl or KCl is commonly required to stabilize ICl. Hence, this means that analogous iodinating reagents such as NaICl$_2$ or KICl$_2$.

U.S. Pat. No. 5,013,865 and U.S. Pat. No. 6,274,762 (Nycomed Imaging AS) describe the general method to prepare NaICl$_2$ or KICl$_2$:

In patent application US 20110020238 (GE HEALTHCARE AS) discloses a process of adding salts such as NaCl or KCl to the aqueous solution of ICl to stabilize it for storage. The method of preparing ICl described in this patent application is shown in the following equation:

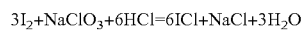

The basis of this method is the use of an oxidant agent to convert iodine to ICl in the present of Cl$^-$. ClO$_3^-$ will be partly reduced to Cl$_2$ as shown in the following equation:

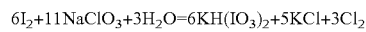

These processes, utilizing ICl, share a common feature in that ICl needs to be pre-prepared prior to reaction. This means that a second corrosion resistant vessel is required in addition to the reaction vessel for the iodination step in order to produce and store ICl. This represents a disadvantage in terms of the cost and the operational arrangement sequence. In addition, the alkali metal halide added to stabilize the iodinating reagent increases the overall content of salt in the product and makes the workup after of the iodination reaction more difficult. The process disclosed in the patent application US 20110021834 (GE HEALTHCARE AS) also does not avoid these drawbacks.

Yet another negative aspect of the ICl type iodination reagents can be gleaned from its reaction mechanism:

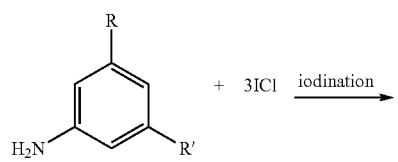

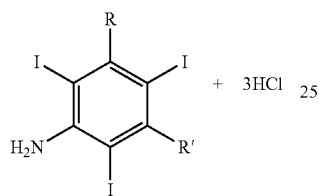

The generation of HCl will lead to a rapid increase of the acidity of the reaction system. This is a serious challenge to the corrosion resistance of the equipment. Furthermore, under high acidity a reaction which generates acid will be going to complete conversion only with difficulty.

Hence it is necessary to use a large excess of the iodination reagent to maintain a reasonable percentage conversion. In addition more diiodinated products can be expected when the conversion is slow thus affecting the quality of the product.

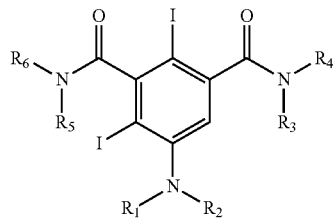

But the worst drawback of ICl type iodinating reagents is that the reagent itself contains a larger amount of chlorine atoms/ions. Chlorine itself can bond to the aromatic nucleus at the high temperature of the process resulting in the introduction of impurities which are chlorinated on the aromatic nucleus. These impurities are subsequently very difficult to be removed in downstream processing. In particular, in either of the two methods to prepare ICl type iodinating reagent system described a small quantity of highly reactive $Cl_2$ will be formed, resulting in formation of chlorinated impurities in the product. The most typical of these chlorinated impurities is the mono-chloro impurity shown as follows:

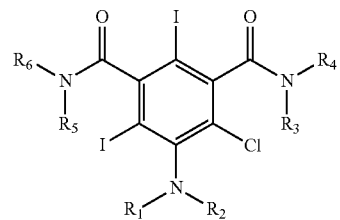

It is therefore necessary to develop new chlorine-free iodinating reagent systems in order to eliminate the adverse effects caused by chlorine in the system. As described above any reagent system which produces a substance which is equivalent to the iodine cation ($I^+$) may be suitably used for poly-iodination of aromatic substrates. Hence, the primary task of developing new iodinating reagent system is designing a system which carries out these types of reactions.

Iodine, being a halogen, requires a strong oxidation system to reach the oxidation number of +1. Besides by preparing iodine mono halides, electrochemistry methods can also achieve this objective. Patent application US 20100331567 (Bracco Research USA Inc.) has disclosed a method to produce triiodinated aromatic compounds by electrochemistry. The essence of this method is to remove an electron from the iodine atom at the electrode in order to form $I^-$ in the reaction system. The positively charged iodine then attacks the substrate to obtain the iodination product.

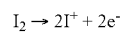

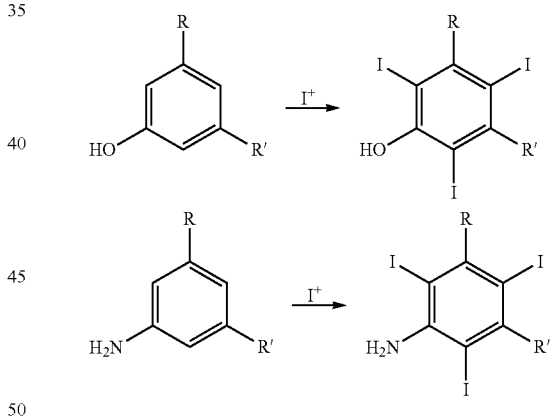

This electrochemical method needs to be developed significantly to surmount many problems before becoming practical at an industrial scale preparation level as the design of industrial scale electrolytic cells is not as easy as the design of a classical stirred tank reaction vessel. In addition the method itself introduces many byproducts into to the product. Notwithstanding, this method does provide guidance for the development of new a chlorine-free iodinating reagent system.

Patent application WO 2010121904 (Bracco Imaging Spa) discloses a process for the preparation of 5-amino-2,4,6-triiodo-isophthalic acid by direct iodination of 5-aminoisophthalic acid using oxidant activated iodine. The preferred oxidant of this process is $HIO_3$, as shown in the following equation:

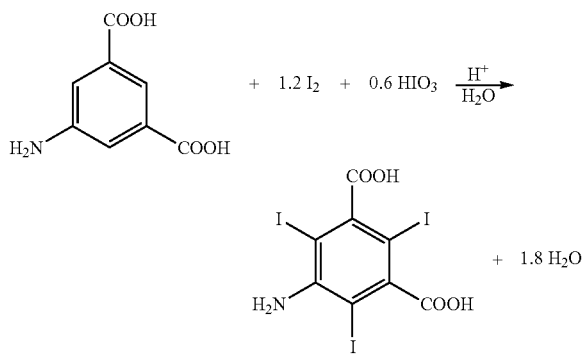

This patent application considers that the mechanism of this reaction involves the iodine cation (I⁺) as the effective iodinating species wherein at least a portion of which is first generated via molecular iodine ($I_2$), whilst the unreactive iodide ion acts as the anionic counter-ion (I⁻). In this way the side product, iodide, is conveniently oxidized by the oxidizing agent back to molecular iodine, or even to iodine cations with a higher oxidation state. Thus all of the iodine is made available for the iodination of the aromatic ring. Thus, the objective of direct iodination of the substrate to obtain the required product using activated iodine is achieved.

Both the method of electrochemistry and the method of activating molecular iodine by oxidation share a fundamental similarity in that the I⁺ iodinating species is generated in situ from molecular iodine. These two methods could be consider as the same type of new iodination reagent systems for the preparation of 3,5-disubstituted-2,4,6-triiodo aromatic amines. Compared with the ICl type iodination reagent system, the difference is in the existence of the activated iodine at the oxidation number of +1 meaning they are not the same. The method which activating iodine by oxidizing conveniently avoids the introducing of chlorine into the reaction system, thereby basically avoiding the formation of monochloro impurities in the product as mentioned above.

All types of iodination reagent systems will form free iodine in the crude product. From an industrial perspective, iodine is relative the most expensive of all of the reactants. However, the above mentioned patent documents rarely discuss the problem of recovering and reusing the excess iodine. In most of the process disclosed in these patent documents, residual iodine was removed by directly adding a reducing agent such as sodium sulfite. This is a drawback when considering the process costs.

In summary, in order to improve the extensively used process utilizing ICl type iodination reagents, two key points should be taken into consideration: controlling the content of partly iodinated species such as diiodinated intermediates in the product; avoiding the formation of chlorinated impurities, such as mono-chloro impurity, which are hard to remove, from the product. In addition, improvement of the yield of the iodination and optimization of the utilization of iodine are also of significant importance.

BRIEF DESCRIPTION OF THE INVENTION

The invention provides a process for the preparation of the compounds of formula (II),

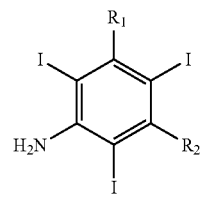

(II)

wherein $R_1$ is independently selected from the group consisting of: carboxyl group (—COOH), carboxylic ester group (—COOR₃) and carboxamido group (—CONH₂, —CONHR₃ or —CONR₄R₅), $R_2$ is independently selected from the group consisting of: carboxylic ester group (—COOR₃) and carboxamido group (—CONH₂, —CONHR₃ or —CONR₄R₅), wherein $R_3$, $R_4$ and $R_5$ are, the same or different from each other, independently a straight or branched $C_1$-$C_4$ alkyl group optionally substituted by one or more, preferably one or two hydroxyl groups, comprising:

a) reacting an iodine oxyacid or the salt thereof with elementary iodine in a solvent under an acidic condition in the presence of an acid or a salt of a strong acid, to generate the iodinating reagent in situ, and in turn reacting the iodinating reagent with compounds of formula (I) added to produce compounds of formula (II),

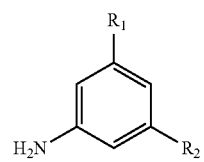

(I)

wherein $R_1$ and $R_2$ are defined as in the formula (II), (b) during the iodination reaction, introducing excessive iodine in vapor form into the reaction system, and then adding a supplementary amount of iodine oxyacid or the salt thereof to the iodination reaction system after a period of reaction time, (c) subliming and collecting the excess free iodine after the iodination reaction is completed, (d) filtering and purifying the crude product of the iodination reaction to obtain the compounds of formula (II), and (e) optionally, recycling the excess free iodine collected after sublimation, the mother liquor of iodination reaction and/or the mother liquor of the purification step to the iodination reaction of step (a).

The iodine oxyacid is iodic acid or periodic acid; and the salt of iodine oxyacid is iodate or periodate, preferably iodate or periodate of an alkali metal, more preferably the iodate of an alkali metal, such as iodate or periodate of sodium or potassium, preferably potassium iodate.

The proportion of the reagents used in the iodinating reaction is in the range where the molar ratio of iodine to the compounds of formula (I) is 0.8/1 to 1.5/1, and in the range where the molar ratio of iodine to iodine oxyacid or the salt thereof is 1/0.2 to 1/0.8.

Preferably, the proportion of the reagents used in the iodinating reaction is in the range where the molar ratio of the compounds of formula (I)/iodine/iodine oxyacid or the salt thereof is 1/1.28/0.64.

The iodine oxyacid or the salt thereof is added in one portion or in several portions.

The acid utilized in step (a) of the process is any substance which can be completely ionized in a protic solvent, or which is transformed to this type of acid in a protic solvent, and which cannot be a halide acid and cannot have notable reducing activity. The acid is selected from the group consisting of sulfuric acid, phosphoric acid, nitric acid, iodic acid, sulfur trioxide, methylsulfonic acid, trifluoroacetic acid or the mixture thereof, preferably sulfuric acid or a mixed acid containing sulfuric acid, more preferably sulfuric acid.

In the process, the range of pH value of the iodination reaction system is 0.5-5, preferably 1-3.

The salt of strong acid used in step (a) may be an alkali metal salt of the strong acid selected from the group consisting of sulfuric acid, phosphoric acid, nitric acid, iodic acid, sulfur trioxide, methylsulfonic acid, trifluoroacetic acid or the mixture thereof, and preferably a sodium or potassium salt of the strong acid, and more preferably sodium sulfate.

The solvent used for the preparation of the iodinating reagent and iodination reaction is a protic solvent, which is selected from the group consisting of water, a $C_1$-$C_4$ low alcohol (for example, methanol, ethanol, propanol, isopropanol, n-butanol or t-butanol), dioxane, glycols (for example, ethylene glycol, propylene glycol or butylene glycol) and aqueous mixtures thereof. The protic solvent is preferably water, a mixture of water and the $C_1$-$C_4$ low alcohol, a mixture of water and dioxane, or a mixture of water and glycols, more preferably water.

In the process, the range of the ratio of the amount of solvent utilized to compounds of formula (I) (w/w) is 20/1 to 2/1, preferably 10/1 to 6/1.

In the process, the compounds of formula (I) are firstly formulated in a solvent to a solution or suspension which are then added to the iodination reaction system in step (a) in one portion or in several portions, and the range of the time of addition is 0.5-24 h, preferably 4-8 h, and wherein the solvent is selected from the group consisting of water, a $C_1$-$C_4$ low alcohol (for example, methanol, ethanol, propanol, isopropanol, n-butanol or t-butanol), dioxane, glycols (for example, ethylene glycol, propylene glycol or butylene glycol) and aqueous mixtures thereof, preferably water, a mixture of water and the $C_1$-$C_4$ low alcohol, a mixture of water and dioxane or a mixture of water and glycols, more preferably water.

The range of the temperature of said iodination reaction is 20° C.-110° C., preferably 40° C.-90° C., more preferably 60° C.-80° C.

The range of the time of said iodination reaction is 2-72 h, preferably 12-48 h, more preferably 16-24 h.

In the process, before filtering in step (d) and during the purification of the crude product obtained in step (d), the internal temperature of the reaction system is cooled to a temperature in the range of 0-20° C., preferably 8-10° C., wherein the purification is carried out by crystallization.

In the process, 1-10 vol of water is added during purification of the crude product followed by stirring for 0.5-5 h within a temperature range of 70-110° C. Preferably, 3-8 vol of water is added during purification of the crude product followed by stirring for 1-2 h within a temperature range of 70-105° C.

An iodine trap is installed in the reaction and purification equipment to recover the sublimed iodine.

In an embodiment of the invention, $R_1$ and $R_2$ are —CONHCH(CH$_2$OH)$_2$.

In an embodiment of the invention, $R_1$ and $R_2$ are —CONHCH$_2$CHOHCH$_2$OH.

DETAILED DESCRIPTION OF THE INVENTION 3,5-disubstituted-2,4,6-triiodo aromatic amines are important intermediates for the preparation of a series of non-ionic contrast agents such as Iopamidol, Iohexol and Iodixanol. Compared with another widely used intermediate 5-amino-2,4,6-triiodo-isophthalic acid which is mentioned in patent application WO 2010121904, 3,5-disubstituted-2,4,6-triiodo aromatic amines are a more cost-efficient choice, because in the synthetic route via this type of intermediates introduces expensive iodine at a later stage of the synthesis resulting in less waste of this expensive material and translating into an economic benefit.

Iodination is the key step in the synthesis of this intermediate. Most iodination processes are based on the traditional ICl type iodination reagent systems. The reaction to prepare ICl is shown in following equation:

$$2I_2+KIO_3+6HCl=5ICl+KCl+3H_2O \text{ or } I_2+Cl_2=2ICl$$

NaCl is also added to the iodination reaction system to convert ICl to a more stable form such as MICl$_2$, wherein M is an alkali metal. There is no doubt that these processes do not avoid the disadvantages of ICl type iodination reagent systems. We have therefore improved this type of processes and developed a new iodination reagent system.

The mechanism of the triiodination reaction of 3,5-disubstitutedanilines in the 2,4,6-positions on the aromatic ring of the substrate is through attack by an electrophilic reagent which is equivalent to I$^+$.

ICl can be recognized as a form of I$^+$ which is stabilized by Cl$^-$, the anion of hydrochloric acid. I$^+$ is generated by de-proportionation of I$_2$ and IO$_3^-$, where only under acidic condition the oxidation potential of IO$_3^-$ is strong enough to initiate this reaction. The role of the HCl is to provide sufficiently acidic conditions and to stabilize the I$^+$. For this reason, if an alternative strong acid could be found to provide acidic condition for the de-proportionation of I$_2$ and IO$_3^-$ as an alternative to HCl, and if the counter anion could also act as a stabilizer of I$^+$ to make the life time of I$^+$ in the reaction system long enough for it to attack the substrate, the ground work of the development of a new iodinating reagent system is achieved.

Considerations based on process costs make sulfuric acid the preferred acidification reagent as it is amongst the common strong acids. The secondary ionization of sulfuric acid is much weaker than its first stage ionization, and hence here sulfuric acid is considered as a strong monoacid to replace HCl thus preparing the iodinating reagent under similar condition. Under the acidity which is required in the iodination reaction H$_2$SO$_4$ exists mainly in the form H$^+$ and HSO$_4^-$. It is therefore reasonable to consider it as a strong monoacid.

Test results indicate that the new iodination reagent system when reacted with 3,5-diamide-2,4,6-triiodo aromatic amines as substrate were promising. We have surprisingly found that the iodination reagent system prepared using H$_2$SO$_4$ instead of HCl gives better iodination results under optimized process condition than the traditional ICl type iodination reagent system.

The key reaction of this new process of the invention is considered to be the following:

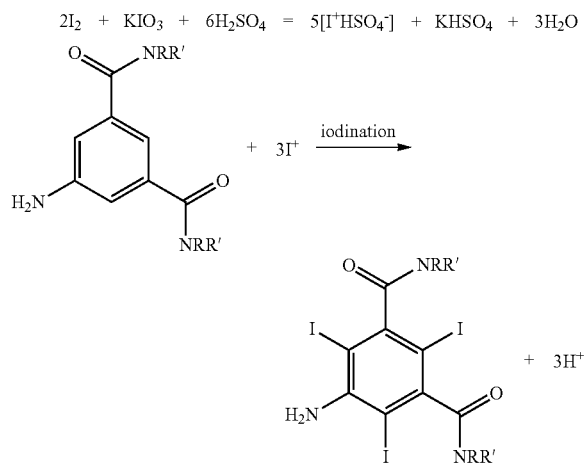

wherein R and R' are defined as in formula (II) for $R_3$, $R_4$ and $R_5$.

[$I^+HSO_4^-$] is descriptive of $I^+$ stabilized by $HSO_4^-$ and does not, necessarily, mean that the concentration of this ion pair is high in solution. However, $I^+$ is sufficiently stabilized by $HSO_4^-$ so its life in the reaction system is long enough to attack the aromatic ring of the substrate to obtain the iodinating product. In the following sections when the proportions in the iodination reaction are described, unless otherwise indicated, all of the said proportions are the molar ratios of this form of iodination reagent ([$I^+HSO_4^-$]) to the substrate.

Summarizing the above, the key reaction of this new process is described in the following equation:

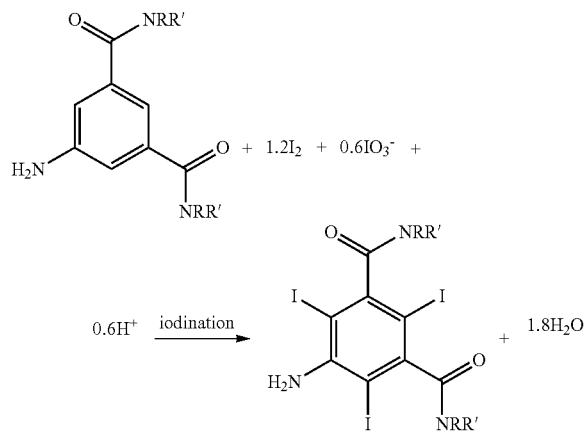

It can be seen from this equation that $H^+$ is consumed in the iodination reaction. In total, 0.6 mol of $H^+$ is consumed during iodination per mol of substrate therefore, acidity does not increase as the reaction progresses as in ICl type iodination reagent systems. Hence there is no tendency for the iodination reaction not to go to completion or to increase the danger of equipment corrosion. To maintain the iodination and to achieve a complete reaction it is only necessary for the amount of $H_2SO_4$ added before the reaction to be equal to the amount of $H^+$ consumed. In addition, as a dibasic acid, secondary ionization of $H_2SO_4$ also helps maintain the acidity of the reaction system, thereby maintain a stable performance of the iodination reagent system.

The new iodination reagent system is tested and verified by experiment. The HPLC test results indicate that mono-chloro impurity could not be detected in the iodination product as to be expected from the application of chlorine-free iodinating reagent system. The content of diiodinated intermediate in the product is lower than 1%. These results are acceptable based on considerations of the requirements for industrial scale preparation. This signifies that the new iodination reagent system can be utilized instead of ICl type iodination reagent systems.

The present invention provides a new iodination process wherein the optimized iodination process conditions bases on the new iodination reagent system described above, the method of recycling the excess iodine after workup and a method of reusing mother liquors from the process. This process can be utilized for industrial scale preparation of 3,5-disubstituted-2,4,6-triiodo aromatic amines. Several disadvantages of the previous ICl type iodination reagent systems are avoided and the quality and yield of the product can be confirmed all at once. This is of significant importance for the industrial preparation of iodinated non-ionic contrast agent.

In the present invention, one example for the preparation of the new iodination reagent system as provided by the present invention is: to water or recycled reaction mother liquor (where the ratio to substrate of formula (I) is 2.5/1 w/w) is added iodine (molar ratio to substrate is 1.28/1), potassium iodate (molar ratio to substrate is 0.59/1) and sodium sulfate (molar ratio to substrate is 0.12/1), followed by slow addition of 98% $H_2SO_4$ (molar ratio to substrate is 0.6/1), stir for 1-1.5 h. The temperature of the system is kept below 50° C., preferably 38-42° C.

In the present invention, one example for adding the solution or suspension of substrate of formula (I) to the iodination reagent system is: add continuously during 4 h with gradual slowing down of the addition rate and with gentle stirring. In the preferred method ¾ of the substrate is added in the first 2 h and ¼ of the substrate is added in the later 2 h.

In the present invention the temperature range of the iodination reaction is suitably 65-70° C., lower than the 90° C. required by the ICl type iodination reagent system.

In the process of the present invention, a supplementary amount of iodine oxyacid or the salt thereof such as $KIO_3$ (it's molar ratio to the substrate is 0.05/1-0.10/1) is required to be added into the iodination reaction system after a period of reaction time such as 10-20 hours, preferably 12-19 h from the complete addition of the substrates in step (a). This portion of iodine oxyacid or the salt thereof such as $KIO_3$ may react with residual iodine in the reaction system to generate a small amount of fresh iodination reagent which promotes total conversion of substrate and diiodinated intermediate thereby effectively reducing the content of diiodinated intermediate in the product. This advantageous effect is achieved if the total iodination reaction time is 16-24 h counting from the time of complete addition of the substrates.

In the present invention the molar ratio of the iodination reagent utilized to the substrate is 3.2/1 (where in the molar ratio of corresponding iodine to substrate is 1.28/1), but in fact a molar ratio of the iodination reagent utilized to the substrate of 3.0/1 (where in the molar ratio of corresponding iodine to substrate is 1.20/1) is enough to iodinate the substrate completely. Iodine is used in excess to guarantee complete iodination, especially for preparation of 5-amino-N,N'-bis-(2,3-dihydroxypropyl)-2,4,6-triiodo-isophthalamide, an intermediate to produce Iohexol and Iodixanol. Given that iodine is relatively expensive among the raw materials used in the process the use of excess iodine is not efficient and is hence detrimental to the economy of the process. A method to efficiently utilize iodine is the installation of an iodine storage container with the reaction vessel is installed and during the first utilization of the equipment an appropriate amount of iodine is added to this storage container. During reaction the storage container is heated to 90-100° C. in order to guarantee that free iodine escaping from the reaction leaves in the gaseous state and that in the wholly interconnected system the iodine in the reaction system and iodine gas above the reaction system is allowed to come into a dynamic equilibrium and free iodine thus can return to the reaction system as the iodine is being consumed in the reaction system. In this way complete triiodination of the substrate is assured. After complete reaction residual iodine escapes from the reaction as a gas state by sublimation, which occurs at an operation temperature of 80-100° C., preferably 85-90° C. This operation can be carried out under normal pressure or under vacuum, preferably under vacuum. Simultaneously the iodine storage container connected to the reaction vessel is cooled by air or a current of water so as to maintain room temperature. This acts as an iodine trap to collect the excess of iodine escaping from the reaction system. The collected iodine establishes a dynamic equilibrium during the next batch of the reaction thus efficiently utilizing all of the iodine. For this reason, the amount of fresh iodine utilized in sequential batches of the reaction is substantially reduced in which the molar ratio of iodine to substrate is reduced to 1.16/1 or even 1.12/1.

After collecting the residual iodine by sublimation the internal temperature of the reaction system is cooled to the range of 0-20° C., preferably 8-12° C., then stir for 12-20 h in order to crystallize of iodination product. The crude product is collected by filtration and the filtrate is also collected as mother liquors. 8 vol of water is added to the crude product, stirred for 1 h at 75-80° C. and then cooled to 8-12° C. Sodium sulfite in a molar ratio to the substrate of 0.06/1 is added to the reaction mixture and stirred for 12-20 h in order to crystallize the product. The iodination product is collected by filtration and the filtrate is also collected as refined mother liquors. The mother liquors from the reaction are concentrated to 2.5/1 w/w with reference to the substrate, whose density is assumed to be equivalent to water. The mother liquors are recycled in the process to prepare the iodination reagent. Mother liquors can normally be recycled for 3-4 cycles. The refine mother liquor can be recycled once in the purification step and then be recycled as the reaction mother liquors.

The wet product obtained after the purification process is dried to constant weight by a normal drying process to afford the final iodination product. The typical molar yield is more than 85%, the content of diiodinated intermediate is no more than 1% and the mono-Cl impurity is not detected by HPLC.

EXAMPLES

The following are non-defining examples to explain the present invention.

When specified, 5-amino-N,N'-bis-(2-hydroxy-1-hydroxymethyl-ethyl)-isophthalamide or 5-amino-N,N'-bis-(2,3-dihydroxypropyl)-isophthalamide, which are the iodination substrates in the following examples, are prepared by know methods such as amidation and reductive hydrogenation of the starting material, dimethyl 5-nitroisophthalate. All of the yields in the following examples are molar yields. These two steps are described in following examples.

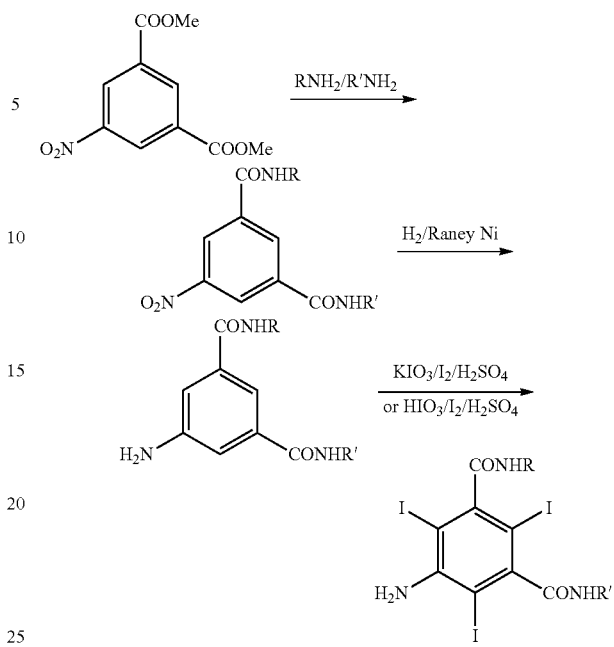

wherein R and R' are defined as in formula (II) for $R_3$.

Preparation of N,N'-Bis-(2-hydroxy-1-hydroxymethyl-ethyl)-5-nitro-isophthalamide

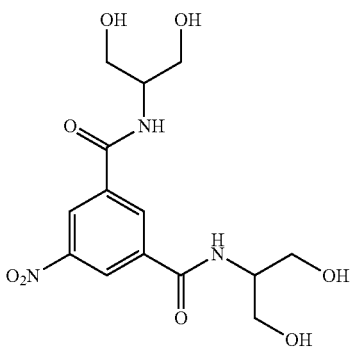 [SMILES: O=C(NC(CO)CO)c1cc(C(=O)NC(CO)CO)cc([N+](=O)[O-])c1]

Dimethyl 5-nitroisophthalate (120 g, 0.5 mol) and serinol (113.6 g, 1.25 mol) are dissolved in methanol (960 mL), and then heated to reflux for 48 h. Cooled to 20° C., the solid is collected filtration using vacuum and the filter cake washed with methanol (50 mL×3). The filter cake is then dried to constant weight to obtain 178.2 g product as a white powder in 99% yield.

Preparation of 5-Amino-N,N'-bis-(2-hydroxy-1-hydroxymethyl-ethyl)-isophthalamide

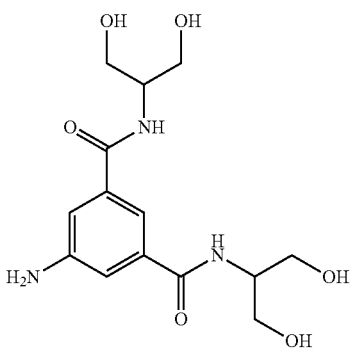

N,N'-Bis-(2-hydroxy-1-hydroxymethyl-ethyl)-5-nitro-isophthalamide (40 g) is dissolved in water (600 mL), and then heated to 90° C. to dissolve. Raney Ni (5 g) is added, and allowed to react for 10 h under a $H_2$ pressure of 1.5 MPa. Raney Ni is removed by filtration and the filter cake washed with 20-30 mL of water. The filtrate and washings are combined to obtain the aqueous solution of 5-Amino-N,N'-bis-(2-hydroxy-1-hydroxymethyl-ethyl)-isophthalamide, which can be utilized directly in the iodination reaction or concentrated and then re-crystallized using methanol to obtain solid product.

Preparation of 5-amino-N,N'-bis-(2,3-dihydroxypropyl)-isophthalamide

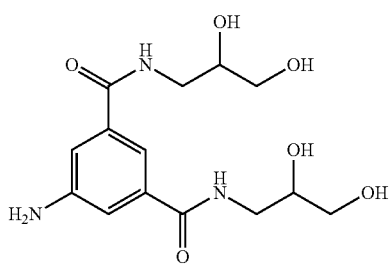 [SMILES: Nc1cc(C(=O)NCC(O)CO)cc(C(=O)NCC(O)CO)c1]

Dimethyl 5-nitroisophthalate (150 g, 0.628 mol) and 3-aminopropane-1,2-diol (143 g, 1.57 mol) is dissolved in methanol (1200 mL), then sodium methoxide (18 g, 0.333 mol) is added, the mixture obtained is stirred for 80 h. The pH is adjusted to 5.5-6.5 using acetic acid, the mixture heated to 40° C. Methanol is removed by distillation initially under normal pressure then under reduced pressure until the mixture is a syrup. Water is added to the mixture to a total volume of 1200 mL to obtain the aqueous solution of N,N'-bis-(2,3-dihydroxypropyl)-2,4,6-triiodo-5-nitro-isophthalamide.

Raney Ni (15 g) is suspended in the aqueous solution (1200 mL) described above, and then reacted for 10 h under a $H_2$ pressure of 1.5 MPa. After reaction is complete, the Raney Ni is removed by filtration, the filter cake washed with water (20 mL×3). The filtrate and washings are combined to obtain aqueous solution of 5-amino-N,N'-bis-(2,3-dihydroxypropyl)-isophthalamide, which can be directly utilized in the iodination reactions described in the following Examples 6 and 7.

Example 1

Preparation of 5-Amino-N,N'-bis-(2-hydroxy-1-hydroxymethyl-ethyl)-2,4,6-triiodo-isophthalamide In a 1000-ml three-necked round-bottom flask is added water (100 mL), iodine (45.1 g, 0.178 mol), potassium iodate (15.6 g, 0.073 mol), anhydrous sodium sulfate (2.1 g, 0.015 mol) are added under mechanical stirring, followed by dropwise addition of 15% $H_2SO_4$ (50 g, 0.076 mol). After 2 h of stirring at 40° C., an aqueous solution of 5-amino-N,N'-bis-(2-hydroxy-1-hydroxymethyl-ethyl)-isophthalamide (380 mL, 0.124 mol) is added at 65° C. during 4 h. After 12 h of reaction at 80° C., additional potassium iodate (2.2 g, 0.010 mol) is added, maintain the temperature and continuing the reaction for 20 h. After reaction is complete, the temperature is increased to sublime residual iodine which is then collected in the iodine trap.

After cooling to 20° C., the solid is collected by using vacuum filtration and the filter cake suspended in water (250 mL), stirred at 80° C. for 1 h. Sodium sulfite (0.3 g, 0.002 mol) is added after cooling to 10° C. and then stirred for 2 h, when the pH of system is adjusted to 6 using 10% NaOH. The solid is collected by filtration under vacuum, the filter cake is washed with a small amount of water (20 mL) and dried to constant weight to obtain 70.0 g of 5-Amino-N,N'-bis-(2-hydroxy-1-hydroxymethyl-ethyl)-2,4,6-triiodo-isophthalamide in 79% yield.

The following are results of several experiments which utilize the new iodination reagent system.

| Batch | Amount of Substrate (g) | Iodinating Reagent/Substrate (molar ratio) | HPLC Results (area %) Diiodinated Intermediate | Mono-Cl Impurity | Reaction Time (h) | Molar Yield (%) |
| --- | --- | --- | --- | --- | --- | --- |
| 1 | 45.8 | 3.2 | 1.69 | Not Detected | 16 | 74.6 |
| 2 | 45.8 | 3.2 | 0.73 | Not Detected | 38 | 78.0 |
| 3 | 41.2 | 3.2 | 0.72 | Not Detected | 48 | 78.8 |

Example 2

Preparation of 5-Amino-N,N'-bis-(2-hydroxy-1-hydroxymethyl-ethyl)-2,4,6-triiodo-isophthalamide In a 1000-ml three-necked round-bottom flask is added water (120 mL), iodine (59.5 g, 0.234 mol), potassium iodate (25.1 g, 0.117 mol), anhydrous sodium sulfate (3 g, 0.021 mol) are added under mechanical stirring, followed by dropwise addition of 15% $H_2SO_4$ (66 g, 0.101 mol). After 2 h of stirring at 40° C., an aqueous solution of 5-amino-N,N'-bis-(2-hydroxy-1-hydroxymethyl-ethyl)-isophthalamide (473 mL, 0.168 mol) is added at 65° C. during 4 h. After 12 h of reaction at 80° C., additional potassium iodate (3 g, 0.014 mol) is added, maintaining the temperature and continuing the reaction for 24 h. After the reaction is complete, the temperature is increased to sublime residual iodine which is then collected in the iodine trap.

After cooling to 20° C., the solid is collected by filtration under vacuum and the filter cake is suspended in water (600 mL) and stirred at 80° C. for 2 h. On cooling to 10° C., the mixture is stirred for 2 h. The solids are collected by suction filtration, the filter cake is washed with a small amount of water (20 mL) and dried to constant weight to obtain 99.2 g of 5-amino-N,N'-bis-(2-hydroxy-1-hydroxymethyl-ethyl)-2,4,6-triiodo-isophthalamide in 84% yield.

Example 3

Preparation of 5-Amino-N,N'-bis-(2-hydroxy-1-hydroxymethyl-ethyl)-2,4,6-triiodo-isophthalamide In a 1000-ml three-necked round-bottom flask is added water (150 mL), followed by dropwise addition of 15% $H_2SO_4$ (66 g, 0.101 mol). Iodine (54.6 g, 0.215 mol), potassium iodate (21.2 g, 0.099 mol), anhydrous sodium sulfate (2.9 g, 0.020 mol) are added under mechanical stirring. After 1.5 h of stirring at 45° C., an aqueous solution of 5-amino-N,N'-bis-(2-hydroxy-1-hydroxymethyl-ethyl)-isophthalamide (440 mL, 0.168 mol) is added at 65° C. during 4 h.

After 19 h of reaction, additional potassium iodate (2.9 g, 0.014 mol) is added, the iodine trap (containing more than 2.6 g of recycled iodine) is connected to the iodination reaction vessel and heated to 90° C. to introduce iodine gas into the reaction. The temperature is maintained at 80° C. and the reaction continued for 24 h. After reaction is complete, the temperature is increased to sublime residual iodine which is then collected in the iodine trap.

Afterwards the mixture is cooled to 8° C. and stirred at this temperature for 4 h. The solid is collected by vacuum filtration and the filter cake suspended in water (480 mL) and stirred at 90° C. for 1 h. Sodium sulfite (1 g, 0.008 mol) is added after cooling to 10° C. and the temperature maintained whilst stirring for 4 h. The solids are collected by vacuum filtration, the filter cake is washed with a small amount of water (25 mL×3) and dried to constant weight to obtain 99.6 g of 5-amino-N,N'-bis-(2-hydroxy-1-hydroxymethyl-ethyl)-2,4,6-triiodo-isophthalamide in 84% yield.

Example 4

Preparation of 5-Amino-N,N'-bis-(2-hydroxy-1-hydroxymethyl-ethyl)-2,4,6-triiodo-isophthalamide In a 1000-ml three-necked round-bottom flask is added concentrated reaction mother liquor recycled from Example 3 (150 mL), followed by dropwise addition of 15% $H_2SO_4$ (66 g, 0.101 mol). Iodine (54.6 g, 0.215 mol), potassium iodate (21.2 g, 0.099 mol) are added under mechanical stirring. After 1.5 h of stirring at 45° C., an aqueous solution of 5-amino-N,N'-bis-(2-hydroxy-1-hydroxymethyl-ethyl)-isophthalamide (440 mL, 0.168 mol) is added at 65° C. during 4 h.

After 19 h of reaction, additional potassium iodate (2.9 g, 0.014 mol) is added, the iodine trap (contains more than 2.6 g of recycled iodine) is collected to the iodination reaction container and heated to 90° C. to introduce iodine gas to the reaction container. The temperature is maintained at 80° C. and the reaction continued for 24 h. After the reaction is complete, the temperature is increased to sublime residual iodine which is then collected in the iodine trap.

Afterwards the mixture is cooled to 8° C. and stirred at this temperature for 4 h, the solids are collected by filtration under vacuum and the filtration cake is suspended with mother liquor (480 mL) from refining step of last batch and stirred at 90° C. for 1 h. Sodium sulfite (1 g, 0.008 mol) is added after cooling to 10° C. and the temperature is maintained whilst stirring for 4 h. The solids are collected by suction filtration, the filter cake is washed with a small amount of water (25 mL×3) and dried to constant weight to obtain 102 g of 5-amino-N,N'-bis-(2-hydroxy-1-hydroxymethyl-ethyl)-2,4,6-triiodo-isophthalamide in 86% yield.

Example 5

Preparation of 5-Amino-N,N'-bis-(2-hydroxy-1-hydroxymethyl-ethyl)-2,4,6-triiodo-isophthalamide In a 1000-ml three-necked round-bottom flask is added water (150 mL), followed by dropwise addition of 15% $H_2SO_4$ (60 g, 0.092 mol). Iodine (46.6 g, 0.183 mol), potassium iodate (19.6 g, 0.092 mol), anhydrous sodium sulfate (2.6 g, 0.018 mol) are added under mechanical stirring. After 1.5 h of stirring at 45° C., 5-amino-N,N'-bis-(2-hydroxy-1-hydroxymethyl-ethyl)-isophthalamide (50 g, 0.153 mol) is dissolved in water to obtain its aqueous solution (440 mL), and then this solution is added to reaction mixture at 65° C. during 4 h.

After 19 h of reaction, additional potassium iodate (2.6 g, 0.012 mol) is added, the iodine trap (contains more than 2.6 g of recycled iodine) is collected to the iodination reaction container and heated to 90° C. to introduce iodine gas to the reaction container. The temperature is maintained at 80° C. and the reaction continued for 24 h. the temperature is increased to sublime residual iodine which is then collected in the iodine trap.

Afterwards the mixture is cooled to 8° C. and stirred at this temperature for 4 h, the solids are collected by filtration under vacuum and the filtration cake is suspended with water (400 mL) and stirred at 90° C. for 1 h. Sodium sulfite (1 g, 0.008 mol) is added after cooling to 10° C. and the temperature is maintained whilst stirring for 4 h. The solids are collected by suction filtration, the filter cake is washed with a small amount of water (25 mL×3) and dried to constant weight to obtain 97 g of 5-amino-N,N'-bis-(2-hydroxy-1-hydroxymethyl-ethyl)-2,4,6-triiodo-isophthalamide in 89.9% yield.

Comparative Example 1

Preparation of 5-Amino-N,N'-bis-(2-hydroxy-1-hydroxymethyl-ethyl)-2,4,6-triiodo-isophthalamide (using ICl type iodinating reagent)

In a 2000-ml three-necked round-bottom flask is added 5-amino-N,N'-bis-(2-hydroxy-1-hydroxymethyl-ethyl)-isophthalamide (91.6 g, 0.280 mol), which is then dissolved in water to obtain its aqueous solution (400 mL), it is then adjusted to pH 4-5 by adding acid and heated to 78-80° C. Previously prepared iodinating reagent ($NaICl_2$, 0.84 mol) is added dropwise to the reaction mixture, the reaction continued for 16 h at 78-80° C. The residual iodine in the reaction system is collected by an iodine trap which equipped with condenser. Afterwards the reaction system is cooled to 10° C. by ice-water bath. The solids are collected by vacuum filtration and the filtrate cake is suspend with water (400 mL) and stirred at 85-90° C. for 1.5 h. The reaction mixture is cooled to 10° C. using ice-water bath, and the temperature is maintained whilst stirring for 2 h. The solids are collected by vacuum filtration, the filtrate cake is washed with little amount of water (20 mL) and dried to constant weight to obtain 146 g, 0.207 mol of iodination product 5-amino-N,N'-bis-(2-hydroxy-1-hydroxymethyl-ethyl)-2,4,6-triiodo-isophthalamide in 74% yield.

Example 6

Preparation of 5-amino-N,N'-bis-(2,3-dihydroxypropyl)-2,4,6-triiodo-isophthalamide In a 1000-ml three-necked round-bottom flask is added water (150 mL), followed by dropwise addition of 15%

H₂SO₄ (65.3 g, 0.100 mol). Iodine (51 g, 0.201 mol), potassium iodate (21.4 g, 0.100 mol), anhydrous sodium sulfate (2.8 g, 0.020 mol) are added under mechanical stirring. After 1.5 h of stirring under 45° C., aqueous solution of 5-amino-N,N'-bis-(2,3-dihydroxypropyl)-isophthalamide (360 mL, 0.167 mol) is added at 65° C. during 4 h.

After 19 h of reaction, additional potassium iodate (2.9 g, 0.014 mol) is added, the iodine trap (contains more than 2.6 g of recycled iodine) is collected to the iodination reaction container and heated to 90° C. to introduce iodine gas to the reaction container. The temperature is maintained at 80° C. and the reaction continued for 24 h. After reaction is complete, the temperature is increased to sublime residual iodine which is then collected in the iodine trap. Activated charcoal (0.5 g) is added to the reaction mixture to decolour it at 90° C. for 1 h, then it is removed by vacuum filtration and the filtrate is collected.

Afterwards the filtrate is cooled to 5° C. and stirred at this temperature for not less than 12 h. The solids are collected by vacuum filtration and the filtrate cake is suspended with water (76 mL). Activated charcoal (0.5 g) is added to the mixture to decolour it at 90° C. for 1 h, then it was removed by hot filtration. The filtrate is collected, and then stirred at 90° C. for 1 h. Sodium sulfite (1 g) is added after cooling to 10° C. and the temperature is maintained whilst stirring for 12 h. The solids are collected by vacuum filtration, the filtrate cake is washed with appropriate amount of water (10 mL) and dried to constant weight to obtain 98 g of 5-amino-N,N'-bis-(2,3-dihydroxypropyl)-2,4,6-triiodo-isophthalamide in 83% yield.

Example 7

Preparation of 5-amino-N,N'-bis-(2,3-dihydroxypropyl)-2,4,6-triiodo-isophthalamide In a 1000-ml three-necked round-bottom flask is added concentrated mother liquor recycled from refining step of Example 6 (120 mL), followed by dropwise addition of 15% H₂SO₄ (65.3 g, 0.100 mol). Iodine (51 g, 0.201 mol), potassium iodate (21.4 g, 0.100 mol) are added under mechanical stirring. After 1.5 h of stirring under 45° C., aqueous solution of 5-amino-N,N'-bis-(2,3-dihydroxypropyl)-isophthalamide (360 mL, 0.167 mol) is added at 65° C. during 4 h.

After 19 h of reaction, additional potassium iodate (2.9 g, 0.014 mol) is added, the iodine trap (contains more than 2.6 g of recycled iodine) is collected to the iodination reaction container and heated to 90° C. to introduce iodine gas to the reaction container. The temperature is maintained at 80° C. and the reaction continued for 24 h. After reaction is complete, the temperature is increased to sublime residual iodine which is then collected in the iodine trap. Activated charcoal (0.5 g) is added to the reaction mixture to decolour it at 90° C. for 1 h and then removed by vacuum filtration. The filtrate is collected.

Afterwards the filtrate is cooled to 5° C. and stirred at this temperature for not less than 12 h. The solids are collected by vacuum filtration and the filtration cake is suspended with water (76 mL), activated charcoal (0.5 g) is added to the mixture to decolour it at 90° C. for 1 h, then it is removed by hot filtration. The filtrate is collected and then stirred at 90° C. for 1 h. Sodium sulfite (1 g) is added after cooling to 10° C., and the temperature is maintained whilst stirring for 12 h. The solids are collected by vacuum filtration, the filtrate cake is washed with appropriate amount of water (10 mL) and dried to constant weight to obtain 101.3 g of 5-amino-N,N'-bis-(2,3-dihydroxypropyl)-2,4,6-triiodo-isophthalamide in 86% yield.

The invention claimed is:
1. A process for the preparation of the compounds of formula (II):

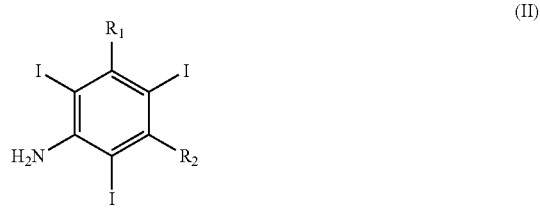

wherein
R₁ is independently selected from the group consisting of: carboxyl group (—COOH), carboxylic ester group (—COOR₃) and carboxamido group (—CONH₂, —CONHR₃ or —CONR₄R₅),
R₂ is independently selected from the group consisting of: carboxylic ester group (—COOR₃) and carboxamido group (—CONH₂, —CONHR₃ or —CONR₄R₅),
wherein R₃, R₄ and R₅ are, the same or different from each other, independently a straight or branched C₁-C₄ alkyl group optionally substituted by one or more hydroxyl groups,
comprising:
a) reacting an iodine oxyacid or the salt thereof with elementary iodine in a solvent under an acidic condition in the presence of an acid or a salt of a strong acid, to generate the iodinating reagent in situ, and in turn reacting the iodinating reagent with compounds of formula (I) added to produce compounds of formula (II),

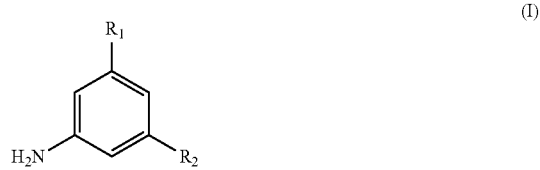

wherein R₁ and R₂ are defined as in the formula (II),
(b) during the iodination reaction, introducing excessive iodine in vapor form into the reaction system, and then adding a supplementary amount of iodine oxyacid or the salt thereof to the iodination reaction system after a period of reaction time,
(c) subliming and collecting the excess free iodine after the iodination reaction is completed,
(d) filtering and purifying the crude product of the iodination reaction to obtain the compounds of formula (II), and
(e) optionally, recycling the excess free iodine collected after sublimation, the mother liquor of iodination reaction and/or the mother liquor of the purification step to the iodination reaction of step (a).
2. A process according to claim 1, wherein said iodine oxyacid is iodic acid or periodic acid; said salt of iodine oxyacid is iodate or periodate, iodate or periodate of an alkali metal.

3. A process according to claim 2, wherein said salt of iodine oxyacid is iodate or periodate of sodium or potassium.

4. A process as claimed in claim 1, wherein the proportion of the reagents used in the iodinating reaction is in the range where the molar ratio of iodine to the compounds of formula (I) is 0.8/1 to 1.5/1, and in the range where the molar ratio of iodine to iodine oxyacid or the salt thereof is 1/0.2 to 1/0.8.

5. A process according to claim 4, wherein said proportion of the reagents used in the iodinating reaction is in the range where the molar ratio of the compounds of formula (I)/iodine/iodine oxyacid or the salt thereof is 1/1.28/0.64.

6. A process according to claim 1, wherein said iodine oxyacid or the salt thereof is added in one portion or in several portions.

7. A process according to claim 1, wherein said acid used in step (a) is selected from the group consisting of: sulfuric acid, phosphoric acid, nitric acid, iodic acid, sulfur trioxide, methylsulfonic acid, trifluoroacetic acid or the mixture thereof; or a mixed acid containing sulfuric acid.

8. A process according to claim 1, wherein said salt of strong acid used in step (a) is an alkali metal salt of the strong acid selected from the group consisting of sulfuric acid, phosphoric acid, nitric acid, iodic acid, sulfur trioxide, methylsulfonic acid, trifluoroacetic acid or the mixture thereof, a sodium or potassium salt of the strong acid, and sodium sulfate.

9. A process according to claim 1, wherein said solvent for the preparation of the iodinating reagent and iodination reaction is a protic solvent, which is selected from the group consisting of water, a $C_1$-$C_4$ low alcohol, dioxane, glycols and aqueous mixtures thereof.

10. A process according to claim 9, wherein said protic solvent is water, a mixture of water and the $C_1$-$C_4$ low alcohol, a mixture of water and dioxane or a mixture of water and glycols.

11. A process according to claim 1, wherein the range of the ratio of the amount of solvent utilized to compounds of formula (I) (w/w) is 20/1 to 2/1.

12. A process according to claim 1, wherein the range of the pH value of the iodination reaction system is 0.5-5.

13. A process according to claim 1, wherein the compounds of formula (I) are firstly formulated in a solvent to a solution or suspension which are then added to the iodination reaction system in one portion or in several portions, and the range of the time of addition is 0.5-24 h, and wherein the solvent is selected from the group consisting of water, a $C_1$-$C_4$ low alcohol, dioxane, glycols and aqueous mixtures thereof, a mixture of water and the $C_1$-$C_4$ low alcohol, a mixture of water and dioxane or a mixture of water and glycols.

14. A process according to claim 1, wherein the range of the temperature of said iodination reaction is 20° C.-110° C.

15. A process according to claim 1, wherein the range of the time of said iodination reaction is 2-72 h.

16. A process according to claim 1, wherein before filtering in step (d) and during the purification of the crude product obtained in step (d), the internal temperature of the reaction system is cooled to a temperature in the range of 0-20° C., wherein the purification is carried out by crystallization.

17. A process according to claim 1, wherein 1-10 vol of water is added during purification of the crude product followed by stirring for 0.5-5 h within a temperature range of 70-110° C.

18. A process according to claim 1, wherein an iodine trap is installed in the reaction and purification equipment to recover the sublimed iodine.

19. A process according to claim 1, wherein $R_1$ and $R_2$ are —CONHCH(CH$_2$OH)$_2$.

20. A process according to claim 1, wherein $R_1$ and $R_2$ are —CONHCH$_2$CHOHCH$_2$OH.

* * * * *